United States Patent
Ishibashi et al.

(10) Patent No.: US 10,138,179 B2
(45) Date of Patent: Nov. 27, 2018

(54) METHOD FOR PRODUCING 2,4-DIENAL ACETAL COMPOUND AND 2,4-DIENAL COMPOUND

(71) Applicant: SHIN-ETSU CHEMICAL CO., LTD., Tokyo (JP)

(72) Inventors: Naoki Ishibashi, Joetsu (JP); Yuki Miyake, Joetsu (JP); Yusuke Nagae, Joetsu (JP); Takeshi Kinsho, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/951,607

(22) Filed: Apr. 12, 2018

(65) Prior Publication Data

US 2018/0305276 A1   Oct. 25, 2018

(30) Foreign Application Priority Data

Apr. 21, 2017   (JP) ................. 2017-084474

(51) Int. Cl.
| | |
|---|---|
| *C07C 45/00* | (2006.01) |
| *C07C 4/10* | (2006.01) |
| *C07C 47/12* | (2006.01) |
| *C07C 11/12* | (2006.01) |

(52) U.S. Cl.
CPC ............... *C07C 4/10* (2013.01); *C07C 11/12* (2013.01); *C07C 45/004* (2013.01); *C07C 47/12* (2013.01)

(58) Field of Classification Search
CPC .............................. C07C 45/004; C07C 47/12
See application file for complete search history.

(56) References Cited

PUBLICATIONS

R. Grée et al., "Fumaraldehyde Monodimethyl Acetal: An Easily Accessible and Versatile Intermediate", Tetrahedron Letters, vol. 27, No. 41, pp. 4983-4986, 1986.
A. Alexakis et al., "Carbocupration of Acetylenic Acetals and Ketals Synthesis of Manicone, Geranial and 2,4 (E,Z)-Dienals" Tetrahedron, vol. 40, No. 4, pp. 715-731, 1984.
Carine Thiot et al., "A One-Pot Synthesis of (E)-Disubstituted Alkenes by a Bimetallic [Rh-Pd]-Catalyzed Hydrosilylation/Hiyama Cross-Coupling Sequence", Chemistry A European Journal, vol. 13, pp. 8971-8978, 2007.
Mohamed Abarbri et al. "Stereospecific Synthesis of (Z) or (E)-3-Methylalk-2-enoic Acids", Tetrahedron Letters, vol. 36, No. 14, pp. 2469-2472, 1995.
Jean Pierre Genêt et al., "Suzuki-Type Cross Coupling Reactions Using Palladium-Water Soluble Catalyst. Synthesis of Functionalized Dienes." Tetrahedron Letters, vol. 36, No. 9, pp. 1443-1446, 1995.

*Primary Examiner* — Sikarl A Witherspoon
(74) *Attorney, Agent, or Firm* — Oliff PLC

(57) ABSTRACT

Methods of producing a 2,4-dienal acetal compound and a 2,4-dienal compound useful as synthesis intermediates of a sex pheromone compound having a conjugated diene structure or a conjugated triene structure. More specifically, a method produces a 2,4-dienal acetal compound of Formula (2): $R^1CH=CH—CH=CH—CH(OR^2)(OR^3)$, including a step of subjecting a 2-enal acetal compound having a leaving group X at position C5 and being expressed by Formula (1): $R^1CHX—CH_2—CH=CH—CH(OR^2)(OR^3)$ to an elimination reaction in the presence of a base to obtain the 2,4-dienal acetal compound (2); and a method for producing a 2,4-dienal compound of Formula (3): $R^1CH=CH—CH=CH—CHO$, further including a step of deprotecting the 2,4-dienal acetal compound (2) to obtain the 2,4-dienal compound (3).

8 Claims, No Drawings

METHOD FOR PRODUCING 2,4-DIENAL ACETAL COMPOUND AND 2,4-DIENAL COMPOUND

BACKGROUND OF THE INVENTION

1. Field of the Invention

The invention relates to methods of producing a 2,4-dienal acetal compound and a 2,4-dienal compound useful as synthesis intermediates of the sex pheromone of an insect.

2. Description of the Related Art

A sex pheromone of insect is a usually bioactive substance secreted by female individuals and having a function of attracting male individuals, and exhibits high attracting activity even in a small amount. A sex pheromone has been used widely as a means for predicting the emergence of insect or finding geological diffusion thereof (emergence into specific areas) or as a means for insect pest control. As the means for insect pest control, control methods called "mass trapping", "lure & kill or attract & kill", "lure & infect or attract & infect", or "mating disruption" have been widely provided for practical use. When a sex pheromone is utilized, economical production of a required amount of the pheromone is necessary for basic research and further for practical application.

Not a few sex pheromones of insects have conjugated diene or conjugated triene structures. For example, it is reported that the sex pheromone of *Ectomyelois ceratoniae* (common name: Carob moth), which is widely distributed throughout the world, omnivorous, and destructive to various crops such as nuts and fruits, is (Z,E)-9,11,13-tetradecatrienal. It is also reported that the sex pheromone of *Cydia pomonella* (common name: Codling moth), which is a crucial insect pest of apples or peaches and is widely distributed throughout the world, is (E,E)-8, 10-dodecadienol.

Examples of the intermediate for producing such a sex pheromone having a conjugated diene or conjugated triene structure include a 2,4-dienal. The conjugated triene structure can be formed by a Wittig reaction between the 2,4-dienal and a phosphorous ylide. The conjugated triene structure can also be formed by converting a 2,4-dienyl halide easily derivable from the 2,4-dienal into the corresponding phosphorous ylide, which is then subjected to a Wittig reaction with an aldehyde. A sex pheromone having a conjugated diene structure can be produced by a nucleophilic substitution reaction of a 2,4-diethyl halide.

Methods of producing a 2,4-dienal from various precursors are known. Of these precursors, a 2,4-dienal acetal compound is particularly excellent. Since the 2,4-dienal acetal compound can provide a 2,4-dienal under mild deprotection conditions and an alcohol produced as a by-product can easily be removed by a liquid separation operation, the 2,4-dienal, though it is unstable, can be obtained efficiently in the absence of a cumbersome purification operation which reduces the yield thereof.

Various methods for producing a 2,4-dienal acetal compound while bypassing an unstable 2,4-dienal have been reported. A 2,4-dienal diethyl acetal is obtained by Alexakis et al. through addition of an alkenyl Gilman reagent to propynal diethyl acetal (Tetrahedron, 40(4), 715(1984)). A 2,4-dienal dimethyl acetal is obtained by Gree et al. through a Wittig reaction after selectively hydrolyzing one of the acetals of fumaraldehyde bis(dimethyl acetal) obtained by addition of bromine to furan in methanol (Tetrahedron Lett. 27, 4983(1986)). A 2,4-dienal acetal compound is obtained by Genet et al. through Suzuki coupling between vinyl iodide and an alkenylboron compound (Tetrahedron Lett. 36, 1443(1995)), by Abarbri et al. through Still coupling between vinyl iodide and an alkenyl tin (Tetrahedron Lett. 36, 2469(1995)), and by Thiot et al through coupling between vinyl iodide and propinal diethyl acetate in the presence of a palladium catalyst, a rhodium catalyst, and silane (Chemistry—A European Journal, 13, 8971(2007)).

SUMMARY OF THE INVENTION

However, the method by Alexakis et al, is not economical because a copper salt of one equivalent or more and an alkenyl lithium of two equivalents or more are necessary. The method by Gree et al. has difficulty in industrial use because in the work-up after preparation of fumaraldehyde bis(dimethyl acetal), a large excess of an inorganic salt should be added in many portions for neutralization, a large amount of salt should be removed by filtration, and a large amount of triphenylphosphine oxide produced as a by-product in the Wittig reaction should be removed. None of the methods by Genet et al., by Abarbri et al. and by Thiot et al. is economical because they require expensive metal catalysts such as palladium and rhodium.

Accordingly, there is a strong demand for the methods for effectively producing a 2,4-dienal acetal compound and a 2,4-dienal compound, the methods being capable of supplying a sufficient amount of sex pheromone compound having a conjugated diene structure or a conjugated triene structure for fundamental biological research or agricultural research of the sex pheromone compound or for application or practical use.

With the foregoing in view, the invention has been made. According to the invention, there are provided the methods for producing a 2,4-dienal acetal compound and a 2,4-dienal compound useful as synthesis intermediates of a sex pheromone compound having a conjugated diene structure or a conjugated triene structure.

With a view to overcoming the above-described problem, the inventors have proceeded with intensive investigation. As a result, it has been found that a 2,4-dienal acetal compound can be synthesized efficiently by subjecting a 2-enal acetal compound having a leaving group at position C5 to an elimination reaction in the presence of a base, leading to the completion of the invention.

In one aspect of the invention, there is provided a method for producing a 2,4-dienal acetal compound of Formula (2):

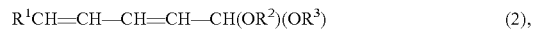

$$R^1CH=CH-CH=CH-CH(OR^2)(OR^3) \quad (2),$$

comprising a step of subjecting a 2-enal acetal compound having a leaving group X at position C5 and being expressed by Formula (1):

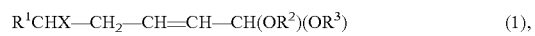

$$R^1CHX-CH_2-CH=CH-CH(OR^2)(OR^3) \quad (1),$$

wherein $R^1$ stands for a hydrogen atom or a substituted or unsubstituted monovalent hydrocarbon group having from 1 to 13 carbon atoms, $R^2$ and $R^3$ each independently stands for a monovalent hydrocarbon group having from 1 to 10 carbon atoms, or $R^2$ and $R^3$ are joined together to form, as $R^2$-$R^3$, a divalent hydrocarbon group having from 2 to 10 carbon atoms, and X stands for a leaving group which is an alkoxy group having from 1 to 12 carbon atoms, an acyloxy group having from 1 to 10 carbon atoms, a silyloxy group having from 3 to 20 carbon atoms, an alkanesulfonyloxy group having from 1 to 10 carbon atoms, an arenesulfonyloxy group having from 6 to 20 carbon atoms, or a halogen atom, to an elimination reaction in the presence of a base to obtain the 2,4-dienal acetal compound (2).

In another aspect of the invention, there is provided a method for producing a 2,4-dienal compound of Formula (3):

$$R^1CH=CH-CH=CH-CHO \qquad (3),$$

comprising the steps of:

subjecting a 2-enal acetal compound having a leaving group X at position C5 and being expressed by Formula (1):

$$R^1CHX-CH_2-CH=CH-CH(OR^2)(OR^3) \qquad (1),$$

wherein $R^1$ stands for a hydrogen atom or a substituted or unsubstituted monovalent hydrocarbon group having from 1 to 13 carbon atoms, $R^2$ and $R^3$ each independently stands for a monovalent hydrocarbon group having from 1 to 10 carbon atoms or $R^2$ and $R^3$ are joined together to form, as $R^2$-$R^3$, a divalent hydrocarbon group having from 2 to 10 carbon atoms, and X stands for a leaving group which is an alkoxy group having from 1 to 12 carbon atoms, an acyloxy group having from 1 to 10 carbon atoms, a silyloxy group having from 3 to 20 carbon atoms, an alkanesulfonyloxy group having from 1 to 10 carbon atoms, an arenesulfonyloxy group having from 6 to 20 carbon atoms, or a halogen atom, to an elimination reaction in the presence of a base to obtain a 2,4-dienal acetal compound of Formula (2):

$$R^1CH=CH-CH=CH-CH(OR^2)(OR^3) \qquad (2); \text{ and}$$

deprotecting the 2,4-dienal acetal compound (2) to obtain the 2,4-dienal compound (3).

According to the invention, a 2,4-dienal acetal compound can be produced efficiently by subjecting a 2-enal acetal compound having a leaving group X at position C5 to an elimination reaction in the presence of a base.

Further, a 2,4-dienal compound can be produced efficiently by deprotecting the 2,4-dienal acetal compound thus obtained.

DETAILED DESCRIPTION OF THE PREFERRED EMBODIMENTS

Some of the chemical formulas of the intermediates, reagents, or intended products described herein may structurally include isomers different in substitution position or stereoisomers such as enantiomers or diastereomers. Any of these chemical formulas stand for all these isomers unless otherwise particularly specified. The isomer may be used singly or in combination of two or more.

First, the step of subjecting a 2-enal acetal compound having a leaving group X at position C5 to an elimination reaction in the presence of a base to produce a 2, 4-dienal acetal compound is described.

The 2-enal acetal compound having a leaving group at position C5 is expressed by Formula (1):

$$R^1CHX-CH_2-CH=CH-CH(OR^2)(OR^3) \qquad (1).$$

In Formula (1), $R^1$ stands for a hydrogen atom or a substituted or unsubstituted monovalent hydrocarbon group having from 1 to 13 carbon atoms, $R^2$ and $R^3$ each independently stands for a monovalent hydrocarbon group having from 1 to 10 carbon atoms, or $R^2$ and $R^3$ are joined together to form, as $R^2$-$R^3$, a divalent hydrocarbon group having from 2 to 10 carbon atoms.

The number of carbon atoms of the unsubstituted or substituted monovalent hydrocarbon group corresponding to $R^1$ is preferably from 1 to 13, more preferably from 1 to 9.

Examples of the monovalent hydrocarbon group corresponding to $R^1$ include a linear saturated hydrocarbon group such as methyl, ethyl, n-propyl, n-butyl, n-pentyl, n-hexyl, n-heptyl, n-octyl and n-nonyl; a branched saturated hydrocarbon group such as isopropyl, isobutyl and isopentyl; a linear unsaturated hydrocarbon group such as vinyl, 1-propenyl, 1-butenyl, 2-propenyl, 2-butenyl, 3-butenyl, 1-propynyl and 2-propynyl; a branched unsaturated hydrocarbon group such as isopropenyl and 2-methyl-2-propenyl; and a cyclic hydrocarbon group such as cyclopropyl, 2-methylcyclopropyl, cyclobutyl and cyclopentyl. A monovalent hydrocarbon group having isomeric relationship with the above-described monovalent hydrocarbon group may also be included, or one or more of the hydrogen atoms of the above-described monovalent hydrocarbon group may be substituted by a methyl group, an ethyl group, or the like.

The number of carbon atoms of the monovalent hydrocarbon group corresponding to $R^2$ or $R^3$ is preferably from 1 to 10, more preferably from 1 to 5.

Examples of the monovalent hydrocarbon group corresponding to $R^2$ or $R^3$ include a linear saturated hydrocarbon group such as methyl, ethyl, n-propyl, n-butyl and n-pentyl; a branched saturated hydrocarbon group such as isopropyl, isobutyl and isopentyl; a linear unsaturated hydrocarbon group such as 2-propenyl and 2-propynyl; a branched unsaturated hydrocarbon group such as 2-methyl-2-propenyl; and a cyclic hydrocarbon group such as cyclopropyl, 2-methylcyclopropyl, cyclobutyl and cyclopentyl. A monovalent hydrocarbon group having isomeric relationship with the above-described hydrocarbon group may also be included, or one or more of the hydrogen atoms of the above-described monovalent hydrocarbon group may be substituted by a methyl group, an ethyl group, or the like.

The monovalent hydrocarbon group corresponding to $R^2$ or $R^3$ is preferably a lower hydrocarbon group (preferably having from 1 to 4 carbon atoms) or primary hydrocarbon group from the standpoint of reactivity in the deprotection or ease of purification because such a hydrocarbon group has high reactivity and a by-product generated by the deprotection can be removed easily by washing with water or concentration. For these reasons, particularly preferable examples of the monovalent hydrocarbon group corresponding to $R^2$ or $R^3$ include methyl, ethyl, and n-propyl.

Next, the embodiment in which $R^2$ and $R^3$ are joined together to form, as $R^2$-$R^3$, a divalent hydrocarbon group having from 2 to 10 carbon atoms is described.

The number of carbon atoms of the divalent hydrocarbon group corresponding to $R^2$-$R^3$ is preferably from 2 to 10, more preferably from 2 to 6.

Examples of the divalent hydrocarbon group corresponding to $R^2$-$R^3$ include a linear saturated hydrocarbon group such as ethylene, 1,3-propylene and 1,4-butylene; a branched saturated hydrocarbon group such as 1,2-propylene, 2,2-dimethyl-1,3-propylene, 1,2-butylene, 1,3-butylene, 2,3-butylene and 2,3-dimethyl-2,3-butylene; a linear unsaturated hydrocarbon group such as 1-vinylethylene and (Z)-2-butene-1,4-diyl; a branched unsaturated hydrocarbon group such as 2-methylene-1,3-propylene; and a cyclic hydrocarbon group such as 1,2-cyclopropylene, 1,2-cyclobutylene, 1,2-cyclopentylene, 1,2-cyclohexylene and 1,2-phenylene. A divalent hydrocarbon group having isomeric relationship with the above-described hydrocarbon group may be included, or one or more of the hydrogen atoms of the above-described divalent hydrocarbon group may be substituted by a methyl group, an ethyl group, or the like.

The divalent hydrocarbon group corresponding to $R^2$-$R^3$ is preferably a lower hydrocarbon group (preferably having from 1 to 4 carbon atoms) from the standpoint of reactivity in the deprotection, ease of purification, and easy availability because such a hydrocarbon group has high reactivity and a by-product generated by the deprotection can be removed easily by washing with water or concentration. For these reasons, particularly preferable examples of the divalent hydrocarbon group corresponding to $R^2$-$R^3$ include ethylene, 1,2-propylene, 1,3-propylene, 1,2-butylene, 1,3-butylene, and 2,3-dimethyl-2,3-butylene.

In Formula (1), X stands for a leaving group which is an alkoxy group having from 1 to 12 carbon atom, an acyloxy group having from 1 to 10 carbon atoms, a silyloxy group having from 3 to 20 carbon atoms, an alkanesulfonyloxy group having from 1 to 10 carbon atoms, an arenesulfonyloxy group having from 6 to 20 carbon atoms, or a halogen atom.

The number of carbon atoms of the alkoxy group corresponding to X is preferably from 1 to 12, more preferably from 1 to 9.

Examples of the alkoxy group corresponding to X include a linear saturated alkoxy group such as methoxy, ethoxy, n-propoxy, n-butoxy and n-pentyloxy; a branched saturated alkoxy group such as isopropoxy and t-butoxy; a linear unsaturated alkoxy group such as 2-propenyloxy and 2-propynyloxy; a branched unsaturated alkoxy group such as 2-methyl-2-propenyloxy; a cyclic alkoxy group such as cyclopropyloxy, 2-methylcyclopropyloxy, cyclobutyloxy and cyclopentyloxy; an aromatic ring-containing alkoxy group such as benzyloxy and paramethoxybenzyloxy; an oxyalkoxy group such as methoxymethoxy, 2-methoxyethoxymethoxy, benzyloxymethoxy, paramethoxybenzyloxymethoxy, 1-ethoxyethoxy and tetrahydropyran-2-yloxy; and a halogenated alkoxy group such as 2,2,2-trichloroethoxy and pentafluoroethoxy. An alkoxy groups having isomeric relationship with the above-described alkoxy group may be included, or one or more of the hydrogen atoms of the above-described alkoxy group may be substituted by a methyl group, an ethyl group, or the like.

Particularly preferable examples of the alkoxy group corresponding to X include methoxy, ethoxy, 2-propenyloxy, methoxymethoxy, and 1-ethoxyethoxy from the standpoint of easy availability and easy removal of a by-product generated by the elimination through washing with water or concentration.

The number of carbon atoms of the acyloxy group corresponding to X is preferably from 1 to 10, more preferably from 1 to 7.

Examples of the acyloxy group corresponding to X include a linear aliphatic acyloxy group such as formyloxy, acetoxy, propanoyloxy, butanoyloxy and crotonyloxy; a branched aliphatic acyloxy group such as 2-methylpropanoyloxy and pivaloyloxy; a halogenated acyloxy group such as trichloroacetoxy and trifluoroacetoxy; and an aromatic acyloxy group such as benzoyloxy. An acyloxy group having isomeric relationship with the above-described acyloxy group may be included, or one or more of the hydrogen atoms of the above-described acyloxy group may be substituted by a methyl group, an ethyl group, or the like.

Particularly preferable examples of the acyloxy group corresponding to X include acetoxy, propanoyloxy, pivaloyloxy, and benzoyloxy from the standpoint of easy availability.

The number of carbon atoms of the silyloxy group corresponding to X is preferably from 3 to 20, more preferably from 3 to 16.

Examples of the silyloxy group corresponding to X include a trialkylsilyloxy group such as trimethylsilyloxy, triethylsilyloxy, triisopropylsilyloxy and t-butyldimethylsilyloxy; and a monoalkyldiarylsilyloxy group such as t-butyldiphenylsilyloxy. A silyloxy group having isomeric relationship with the above-described silyloxy group may be included, or one or more of the hydrogen atoms of the above-described silyloxy group may be substituted by a methyl group, an ethyl group, or the like.

Particularly preferable examples of the silyloxy group corresponding to X include trimethylsilyloxy group and triethylsilyloxy group from the standpoint of easy availability and easy removal of a by-product generated by the elimination through concentration.

The number of carbon atoms of the alkanesulfonyloxy group corresponding to X is preferably from 1 to 10, more preferably from 1 to 8.

Examples of the alkanesulfonyloxy group corresponding to X include methanesulfonyloxy, ethanesulfonyloxy, 1-butanesulfonyloxy, 1-octanesulfonyloxy, allylsulfonyloxy, 10-camphor-sulfonyloxy, trifluoromethanesulfonyloxy, and benzylsulfonyloxy. An alkanesulfonyloxy group having isomeric relationship with the above-described alkanesulfonyloxy group may be included, or one or more of the hydrogen atoms of the above-described alkanesulfonyloxy group may be substituted by a methyl group, an ethyl group, or the like.

Particularly preferable examples of the alkanesulfonyloxy group corresponding to X include methanesulfonyloxy and ethanesulfonyloxy from the standpoint of easy availability.

The number of carbon atoms of the arenesulfonyloxy group corresponding to X is preferably from 6 to 20, more preferably from 6 to 15.

Examples of the arenesulfonyloxy group corresponding to X include benzenesulfonyloxy, 4-chlorobenzenesulfonyloxy, 4-methoxybenzenesulfonyloxy, 2-nitrobenzenesulfonyloxy, 2,4,6-trimethylbenzenesulfonyloxy, paratoluenesulfonyloxy, 1-naphthalenesulfonyloxy, and 2-naphthalenesulfonyloxy. An arenesulfonyloxy group having isomeric relationship with the above-described arenesulfonyloxy group may be included, or one or more of the hydrogen atoms of the above-described arenesulfonyloxy group may be substituted by a methyl group, an ethyl group, or the like.

Particularly preferable examples of the arenesulfonyloxy group corresponding to X include benzenesulfonyloxy and paratoluenesulfonyloxy from the standpoint of easy availability.

Examples of the halogen atom corresponding to X include fluorine, chlorine, bromine, and iodine.

Particularly preferable examples of the halogen atom corresponding to X include chlorine and bromine from the standpoint of easy availability.

The 2-enal acetal compound having a leaving group X at position C5 does not need conversion of this leaving group into another leaving group having high leaving ability and can be subjected to an elimination reaction as it is, when the leaving group X has not only high leaving ability such as an alkanesulfonyloxy group, an arenesulfonyloxy group or a halogen atom but also low leaving ability such as an alkoxy group, an acyloxy group or a silyloxy group. It is because acidity at position C4 of the 2-enal acetal compound having a leaving group X at position C5 is enhanced due to an electronic influence of the acetal group.

The 2-enal acetal compound having the low-leaving-ability leaving group X at position C5, such as an alkoxy group, an acyloxy group or a silyloxy group, has high thermal stability compared with the 2-enal acetal compound having an alkanesulfonyloxy group, an arenesulfonyloxy group or a halogen atom, so that purification can be carried out easily by industrially advantageous distillation.

On the other hand, a substrate having a hydrocarbon group instead of the acetal group does not have enhanced acidity at position C4 so that the elimination reaction does not proceed efficiently particularly when a leaving group having low leaving ability such as an alkoxy group, an acyloxy group or a silyloxy group is used.

Examples of a geometric isomer of the 2-enal acetal compound having a leaving group X at position C5 include an (E)-2-enal acetal compound and a (Z)-2-enal acetal compound.

The compound having a hydrogen atom as $R^1$ is a pentenal acetal compound.

The 2-enal acetal compound (1) having a leaving group X at position C5 may be produced by making use of a known method. For example, a Z-isomer of the 2-enal acetal compound (1) having a leaving group X at position C5 may be selectively produced by hydrogenating the triple bond of a 2-ynal acetal compound having a leaving group X at position C5 and being expressed by Formula (4), while an E-isomer of the 2-enal acetal compound (1) having a leaving group X at position C5 may be selectively produced by reducing the triple bond to a double bond by hydrosilylation and desilylation. In the scheme below, $R^1$, $R^2$ and $R^3$ have the same meanings as those described above, respectively.

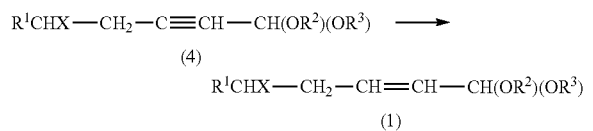

According to the invention, the elimination reaction proceeds by deprotonation at position C4 of the 2-enal acetal compound of Formula (1) and having a leaving group X at position C5 in the presence of a base. The geometry at position C2 is therefore retained before and after the reaction. This means that a (2E)-2,4-dienal acetal compound can be obtained from the E isomer of the 2-enal acetal compound having a leaving group X at position C5 and a (2Z)-2,4-dienal acetal compound can be obtained from the Z isomer. In the scheme below, $R^1$, $R^2$ and $R^3$ have the same meanings as those described above, respectively.

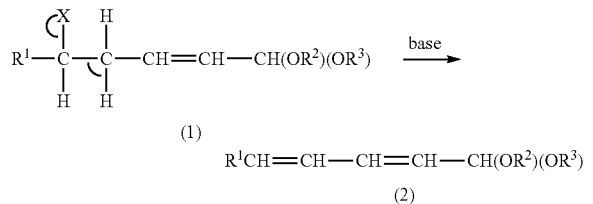

The elimination reaction is considered to proceed according to E2 elimination mechanism. In E2 elimination, it is most advantageous that the reaction proceeds via the conformation in which the hydrogen atom at position C4 and the leaving group X at position C5 as well as the vinyl group at position C4 and $R^1$ at position C5 both are in an antiperiplanar relationship. As a result, a geometric isomer having E as the geometry at position C4 is provided preferentially. On the other hand, it is next advantageous that the reaction proceeds via the conformation in which the hydrogen atom at position C4 and the leaving group X at position C5 are in an antiperiplanar relationship, while the vinyl group at position C4 and $R^1$ at position C5 are in a gauche relationship. As a result, a geometric isomer having Z as the geometry at the 4-position is provided.

Examples of the base to be used for the elimination reaction include a metal alkoxide such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide and potassium t-amyloxide; an organometallic reagent such as methyllithium, ethyllithium, n-butyllithium, methylmagnesium chloride and dimsyl sodium; a metal amide such as sodium amide, lithium amide, lithium diisopropylamide, lithium hexamethyldisilazide, sodium hexamethyldisilazide, potassium hexamethyldisilazide and lithium dicyclohexylamide; a metal hydride such as sodium hydride, potassium hydride and calcium hydride; and an amine such as triethylamine, piperidine, pyrrolidine, pyridine, 4-dimethylaminopyridine and 1,8-diazabicyclo[5.4.0]-7-undecene. The base may be selected in view of the kind of the substrate, reactivity, or selectivity.

The amount of the base to be used for the elimination reaction is preferably from 0.6 to 3 mol, more preferably from 0.7 to 2 mol, still more preferably from 0.8 to 1.5 mol per mol of the 2-enal acetal compound (1) having a leaving group X at position C5 from the standpoint of the yield and economy.

Examples of the solvent to be used for the elimination reaction include ethers such as diethyl ether, dibutyl ether, tetrahydrofuran and 1,4-dioxane; hydrocarbons such as hexane, heptane, benzene, toluene, xylene and cumene; chlorine-based solvents such as methylene chloride, chloroform and trichloroethylene; aprotic polar solvents such as N,N-dimethylformamide, 1,3-dimethyl-2-imidazolidinone, dimethyl sulfoxide and hexamethylphosphoric triamide; nitriles such as acetonitrile and propionitrile; esters such as ethyl acetate and n-butyl acetate; and alcohols such as methanol, ethanol and t-butyl alcohol. The solvent may be used singly or in combination of two or more.

The amount of the solvent to be used for the elimination reaction is preferably from 0 to 10,000 g, more preferably from 0 to 5,000 g per mol of the 2-enal acetal compound (1) having a leaving group X at position C5.

When the metal alkoxide, organometallic reagent, metal amide, or metal hydride is used as the base, the reaction temperature of the elimination reaction is preferably from −78 to 50° C., more preferably from −50 to 40° C., still more preferably from −30 to 30° C. from the standpoint of the yield.

When the amine is used as the base, the reaction temperature of the elimination reaction is preferably from 0 to 180° C., more preferably from 10 to 150° C., still more preferably from 20° to 130° C.

The reaction time of the elimination reaction may be selected freely. It is preferable from the standpoint of the yield to monitor the reaction by gas chromatography (GC) or silica gel thin-layer chromatography (TLC) and complete the reaction. It is typically from about 0.5 to 24 hours.

Examples of the geometric isomer of the 2,4-dienal acetal compound having a hydrogen atom as $R^1$ include a (2E)-2,4-pentadienal acetal compound and a (2Z)-2,4-pentadienal acetal compound.

Examples of the geometric isomer of the 2,4-dienal acetal compound (2) having, as $R^1$, a substituted or unsubstituted monovalent hydrocarbon group having from 1 to 13 carbon atoms include a (2E,4E)-2,4-dienal acetal compound, a (2E,4Z)-2,4-dienal acetal compound, a (2Z,4E)-2,4-dienal acetal compound, and a (2Z,4Z)-2,4-dienal acetal compound.

Next, a step of deprotecting the 2,4-dienal acetal compound (2) to obtain a 2,4-dienal compound (3) is described.

Examples of the deprotection include deprotection by a hydrolysis reaction and deprotection by a nucleophilic substitution reaction.

First, deprotection by a hydrolysis reaction is described.

Examples of an acid to be used for deprotection by a hydrolysis reaction include an inorganic acid and a salt thereof such as hydrochloric acid, hydrobromic acid, hydroiodic acid, sulfuric acid, nitric acid, phosphoric acid and salts thereof; an organic acid and a salt thereof such as formic acid, acetic acid, propionic acid, oxalic acid, trifluoroacetic acid, methanesulfonic acid, benzenesulfonic acid, p-toluenesulfonic acid, naphthalenesulfonic acid and salts thereof; Lewis acid such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide and trimethyliodosilane; an oxide such as alumina, silica gel and titania; and a mineral such as montmorillonite. The acid may be used singly or in combination of two or more.

The amount of the acid to be used for the deprotection by a hydrolysis reaction is preferably small from the standpoint of economy. It may be selected freely insofar as a reaction rate adequate for practical use can be attained. It is preferably from 0.00001 to 10,000 mol, more preferably from 0.0001 to 1,000 mol, still more preferably from 0.001 to 100 mol per mol of the 2,4-dienal acetal compound serving as a substrate.

Examples of the solvent to be used for the deprotection by a hydrolysis reaction include ethers such as diethyl ether, dibutyl ether, tetrahydrofuran and 1,4-dioxane; hydrocarbons such as hexane, heptane, benzene, toluene, xylene and cumene; chlorine-based solvents such as methylene chloride, chloroform and trichloroethylene; ketones such as acetone and 2-butanone; aprotic polar solvents such as N,N-dimethylformamide, 1,3-dimethyl-2-imidazolidinone, dimethyl sulfoxide and hexamethylphosphoric triamide; nitriles such as acetonitrile and propionitrile; esters such as ethyl acetate and n-butyl acetate; and alcohols such as methanol, ethanol and t-butyl alcohol. The solvent may be used singly or in combination of two or more.

The amount of the solvent to be used for the deprotection by a hydrolysis reaction is preferably from 0 to 10,000 g per mol of the 2,4-dienal acetal compound.

Regarding an amount of water to be added for the deprotection by a hydrolysis reaction, the larger amount of water is more advantageous because the equilibrium shifts to the aldehyde formation side. However, the amount of water is preferably from 1 to 10,000 mol, more preferably from 1 to 1,000 mol, still more preferably from 1 to 500 mol per mol of the 2,4-dienal acetal compound in consideration of economy, working efficiency, the yield and the like.

In the deprotection by a hydrolysis reaction, a 2,4-dienal compound maintaining the geometric structure of the starting material 2,4-dienal acetal compound can be produced by adjusting the pH of the aqueous solution in the reaction system at preferably more than 1.0, more preferably more than 1.0 and less than 7.0, still more preferably 2.0 or more and 6.0 or less. On the other hand, by adjusting the pH of the aqueous solution in the reaction system at preferably 1 or less, more preferably −1.0 or more and 1.0 or less, still more preferably 0 or more and 1.0 or less, the isomerization proceeds and a (2E,4E)-2,4-dienal compound is obtained selectively irrespective of the geometric structure at positions C2 and C4 of the starting material 2,4-dienal acetal compound.

The pH value can be measured, for example, with pH test paper or a pH meter while setting the temperature of a liquid to be measured at 25° C.

The reaction temperature of the deprotection by a hydrolysis reaction is preferably from −78 to 160° C., more preferably from −50 to 140° C., still more preferably from −30 to 120° C., though depending on the reaction conditions.

The reaction time of the deprotection by a hydrolysis reaction may be selected freely. It is preferable to monitor the reaction by gas chromatography (GC) or silica gel thin-layer chromatography (TLC) and complete the reaction from the standpoint of the yield. It is typically from about 0.5 to 24 hours.

The reaction may be carried out while removing an alcohol generated by the hydrolysis of the acetal compound from the reaction system by a method such as distillation or layer separation.

Next, deprotection by a nucleophilic substitution reaction is described.

Examples of a nucleophilic reagent to be used for the deprotection by a nucleophilic substitution reaction include a metal halide salt such as lithium iodide, sodium iodide, potassium iodide, titanium tetrachloride and zinc chloride; a boron halide such as boron tribromide and bromodimethylborane; and a silicon halide such as iodotrimethylsilane and bromotrimethylsilane. The nucleophilic reagent may be used singly or in combination of two or more.

The amount of the nucleophilic reagent to be used for the deprotection by a nucleophilic substitution reaction is preferably from 0.6 to 20 mol, more preferably from 0.7 to 10 mol, still more preferably from 0.8 to 5 mol per mol of the substrate 2,4-dienal acetal compound.

Examples of the solvent to be used for the deprotection by a nucleophilic substitution reaction include ethers such as diethyl ether, dibutyl ether, tetrahydrofuran and 1,4-dioxane; hydrocarbons such as hexane, heptane, benzene, toluene, xylene and cumene; chlorine-based solvents such as methylene chloride, chloroform and trichloroethylene; ketones such as acetone and 2-butanone; aprotic polar solvents such as N,N-dimethylformamide, 1,3-dimethyl-2-imidazolidinone, dimethyl sulfoxide and hexamethylphosphoric triamide; nitriles such as acetonitrile and propionitrile; esters such as ethyl acetate and n-butyl acetate; and alcohols such as methanol, ethanol and t-butyl alcohol, The solvent may be used singly or in combination of two or more.

The amount of the solvent to be used for the deprotection by a nucleophilic substitution reaction is preferably from 0 to 10,000 g per mol of the 2,4-dienal acetal compound.

The reaction temperature of the deprotection by a nucleophilic substitution reaction is preferably from −78 to 160° C., more preferably from −50 to 140° C., still more preferably from −30 to 120° C., though depending on the reaction conditions.

The reaction time of the deprotection by a nucleophilic substitution reaction may be selected freely. It is preferable to monitor the reaction by gas chromatography (GC) or silica gel thin-layer chromatography (TLC) and complete the reaction from the standpoint of the yield. It is typically from about 0.5 to 24 hours.

As described above, there are provided convenient and efficient methods of producing a 2,4-dienal acetal compound and a 2,4-dienal compound, which are useful as intermediates.

EXAMPLES

The invention will hereinafter be described in further detail by Examples. It should not be construed that the invention is limited by or to them.

A sample for the measurement of the spectrum of a compound is obtained by purifying a crude product if necessary. The term "crude yield" means a yield calculated without purification.

Example 1

Production No. 1 of
(Z)-5,5-diethoxy-1,3-pentadiene (2)

In a nitrogen atmosphere, potassium t-butoxide (169 g, 1.51 mol) and DMF (467 g) were placed in a reactor, stirred at from 0 to 5° C., subjected to dropwise addition of (Z)-5,5-diethoxy-3-pentenyl methoxymethyl ether (262 g, 1.20 mol) at from 0 to 10° C., and then stirred at room temperature for 20 hours. After addition of water to the reaction product mixture, the resulting mixture was extracted with hexane. The organic phase thus separated was subjected to conventional work-up including washing, drying, and concentration, followed by distillation under reduced pressure to obtain intended (Z)-5,5-diethoxy-1,3-pentadiene (2) (187 g, 1.07 mol) in a yield of 89%.

(Z)-5,5-Diethoxy-1,3-pentadiene (2)

Colorless to Light Yellow Oily Liquid
IR (D-ATR): ν=3088, 2976, 2930, 2880, 1595, 1482, 1444, 1373, 1325, 1291, 1123, 1055, 1002, 911, 841, 793, 604, 534 cm$^{-1}$.
$^1$H-NMR (500 MHz, CDCl$_3$): δ=1.17-1.22 (6H, t, J=7.1 Hz), 3.46-3.54 (2H, m), 3.61-3.67 (2H, m), 5.20 (1H, d, J=10.3 Hz), 5.25-5.28 (1H, m), 5.31 (1H, dd, J=1.1, 6.5 Hz), 5.47 (1H, dd, J=6.3, 11.3 Hz), 6.15 (1H, t, J=11.3 Hz), 6.68-6.76 (1H, m) ppm.
$^{13}$C-NMR (125 MHz, CDCl$_3$): δ=15.18, 60.53, 97.69, 120.08, 128.47, 131.87, 132.53 ppm.

Example 2

Production No. 2 of
(Z)-5,5-diethoxy-1,3-pentadiene (2)

(Z)-5,5-diethoxy-1,3-pentadiene (2) (143 g, 1.02 mol) was obtained in a yield of 85% in the same mariner as in Example 1 except for the use of a tetrahydrofuran solution of sodium hexamethyldisilazide (1.9 mol/l, 795 ml, 1.51 mol) instead of potassium t-butoxide (169 g, 1.51 mol).

Example 3

Production of (E)-5,5-diethoxy-1,3-pentadiene (2)

(E)-5,5-diethoxy-1,3-pentadiene (2) (161 g, 1.03 mol) was obtained in a yield of 86% in the same manner as in Example 1 except for the use of (E)-5,5-diethoxy-3-pentenyl methoxymethyl ether (262 g, 1.20 mol) instead of (Z)-5,5-diethoxy-3-pentenyl methoxymethyl ether (262 g, 1.20 mol).

(E)-5,5-Diethoxy-1,3-pentadiene (2)

Colorless to Light Yellow Oily Liquid
$^1$H-NMR (500 MHz, CDCl$_3$): δ=1.20 (6H, t, J=7.1 Hz), 3.41-3.52 (2H, m), 3.60-3.66 (2H, m), 4.93 (1H, d, J=4.6 Hz), 5.14 (1H, dd, J=1.4, 14.1 Hz), 5.24-5.27 (1H, m), 5.67 (1H, dd, J=5.2, 14.6 Hz), 6.29-6.37 (2H, m) ppm.
$^{13}$C-NMR (125 MHz, CDCl$_3$): δ=15.17, 60.92, 100.93, 118.76, 130.51, 133.53, 135.90 ppm.

Example 4

Production of (E)-2-buta-1,3-dienyl-4-methyl-1,3-dioxolane (2)

(E)-2-buta-1,3-dienyl-4-methyl-1,3-dioxolane (2) (143 g, 1.02 mol) was obtained in a yield of 85% in the same manner as in Example 1 except for the use of (E)-2-(4-methoxymethoxy-1-butenyl)-4-methyl-1,3-dioxolane (243 g, 1.20 mol) instead of (Z)-5,5-diethoxy-3-pentenyl methoxymethyl ether (262 g, 1.20 mol).

(E)-2-Buta-1,3-dienyl-4-methyl-1,3-dioxolane (2)

Colorless to Light Yellow Oily Liquid
$^1$H-NMR (500 MHz, CDCl$_3$): δ=1.27 (1.5H, d, J=6.1 Hz), 1.31 (1.5H, d, J=6.1 Hz), 3.41 (0.5H, t, J=7.5 Hz), 3.46 (0.5H, t, J=7.5 Hz), 3.99 (0.5H, dd, J=6.3, 7.6 Hz), 4.13 (0.5H, dd, J=5.9, 7.6 Hz), 4.15-4.29 (1H, m), 5.17-5.20 (1H, m), 5.27-5.34 (1.5H, m), 5.42 (0.5H, d, J=6.1 Hz), 5.63-5.72 (1H, m), 6.30-6.42 (2H, m) ppm.

Example 5

Production No. 1 of
(Z)-5,5-dimethoxy-1,3-pentadiene (2)

In a nitrogen atmosphere, (Z)-5,5-dimethoxy-3-pentenyl benzoate (1.03 g, 4.12 mmol) and THF (33 g) were placed in a reactor, stirred at from 0 to 5° C., subjected to dropwise addition of a toluene solution of potassium hexamethyldisilazide (0.5 mol/l, 12.4 ml, 6.18 mmol) at from 0 to 10° C., and then stirred at from 0 to 10° C. for 3 hours. After addition of water to the reaction product mixture, the resulting mixture was extracted with ether. The organic phase thus separated was subjected to conventional work-up including washing, drying, and concentration to obtain intended (Z)-5,5-dimethoxy-1,3-pentadiene (2) (0.422 g, 3.30 mmol) in a crude yield of 80%.

(Z)-5,5-Dimethoxy-1,3-pentadiene (2)

Colorless to Light Yellow Oily Liquid
$^1$H-NMR (500 MHz, CDCl$_3$): δ=3.27 (3H, s), 5.14 (1H, dd, J=1.6, 6.2 Hz), 5.17-5.26 (2H, m), 5.37 (1H, dd, J=6.1, 11.1 Hz), 6.14 (1H, dt, J=0.8, 11.8 Hz), 6.61-6.69 (1H, m) ppm.

Example 6

Production No. 2 of
(Z)-5,5-dimethoxy-1,3-pentadiene (2)

In a nitrogen atmosphere, potassium t-butoxide (3.35 g, 29.9 mmol) and DMF (20 g) were placed in a reactor, stirred at from 0 to 5° C., subjected to dropwise addition of (Z)-ethyl 5,5-dimethoxy-3-pentenyl ether (3.48 g, 20.0 mmol) at from 0 to 10° C., and then stirred at room temperature for 3 hours. After addition of water to the reaction product mixture, the resulting mixture was extracted with ether. The organic phase thus separated was subjected to conventional work-up including washing, drying, and concentration to obtain intended (Z)-5,5-dimethoxy-1,3-pentadiene (2) (1.92 g, 15.0 mmol) in a crude yield of 75%.

Example 7

Production No. 3 of (Z)-5,5-dimethoxy-1,3-pentadiene (2)

(Z)-5,5-dimethoxy-1,3-pentadiene (2) (2.08 g, 16.2 mmol) was obtained in a crude yield of 81% in the same manner as in Example 5 except for the use of (Z)-5,5-dimethoxy-3-pentenyloxytrimethylsilane (4.37 g, 20.0 mmol) instead of (Z)-ethyl 5,5-dimethoxy-3-pentenyl ether (3.48 g, 20.0 mmol).

Example 8

Production No. 4 of (Z)-5,5-dimethoxy-1,3-pentadiene (2)

(Z)-5,5-dimethoxy-1,3-pentadiene (2) (2.08 g, 16.2 mmol) was obtained in a crude yield of 81% in the same manner in Example 5 except for the use of (Z)-5,5-dimethoxy-3-pentenyl methanesulfonate (4.49 g, 20.0 mmol) instead of (Z)-ethyl 5,5-dimethoxy-3-pentenyl ether (3.48 g, 20.0 mmol).

Example 9

Production No. 5 of (Z)-5,5-dimethoxy-1,3-pentadiene (2)

(Z)-5,5-dimethoxy-1,3-pentadiene (2) (2.05 g, 16.0 mmol) was obtained in a crude yield of 80% in the same manner as in Example 5 except for the use of (Z)-5-chloro-1,1-dimethoxy-3-pentene (3.29 g, 20.0 mmol) instead of (Z)-ethyl 5,5-dimethoxy-3-pentenyl ether (3.48 g, 20.0 mmol).

Example 10

Production No. 1 of 1,1-diethoxy-2,4-hexadiene (2)

In a nitrogen atmosphere, (Z)-6,6-diethoxy-4-hexen-2-yl methanesulfonate (260 mg, 0.976 mmol), DBU (220 mg, 1.45 mmol) and toluene (4 g) were placed in a reactor, and stirred under heating and refluxing for 5 hours. After addition of water to the reaction product mixture, the organic phase thus separated was subjected to conventional work-up including washing, drying, and concentration to obtain intended 1,1-diethoxy-2,4-hexadiene (2) (122 mg, 0.781 mmol) as a 2Z4E:2Z4Z=73:27 geometric isomer mixture in a crude yield of 80%.

1,1-Diethoxy-2,4-hexadiene (2)

Colorless to Light Yellow Oily Liquid
$^1$H-NMR (500 MHz, CDCl$_3$): δ=1.18-1.24 (6H, m), 1.78 (3H, dd, J=1.5, 6.9 Hz), 3.46-3.54 (2H, m), 3.61-3.68 (2H, m), 5.29-5.34 (2H, m), 5.77 (1H, dd, J=7.0, 14.9 Hz), 6.08-6.14 (1H, m), 6.33-6.50 (1H, m) ppm (ZE isomer).

Example 11

Production No. 2 of 1,1-diethoxy-2,4-hexadiene (2)

In a nitrogen atmosphere, potassium t-butoxide (1.68 g, 15.0 mmol) and DMF (50 g) were placed in a reactor, stirred at from 0 to 5° C., subjected to dropwise addition of (Z)-6,6-diethoxy-4-hexen-2-yl methoxymethyl ether (2.58 g, 11.1 mmol) at from 0 to 10° C., and then stirred at room temperature for 20 hours. After addition of water to the reaction product mixture, the resulting mixture was extracted with ether. The organic phased thus separated was subjected to conventional work-up including washing, drying, and concentration to obtain intended 1,1-diethoxy-2,4-hexadiene (2) (1.23 g, 7.22 mmol) as a 2Z4E:2Z4Z=73:27 geometric isomer mixture in a crude yield of 65%.

As shown in Examples 1 to 11, a 2,4-dienal acetal compound can be produced efficiently by subjecting a 2-enal acetal compound having a leaving group at position C5 to an elimination reaction in the presence of a base. Even if the leaving group has low leaving ability such as alkoxy group, acyloxy group or silyloxy group, the elimination reaction is allowed to proceed under mild conditions.

Comparative Example 1

Production of (E)-1,3-tetradecadiene

In a nitrogen atmosphere, potassium t-butoxide (1.69 g, 15.1 mmol) and DMF (4.7 g) were placed in a reactor, stirred at from 0 to 5° C., subjected to dropwise addition of (E)-3-tetradecadienyl methoxymethyl ether (3.08 g, 12.0 mmol) at from 0 to 10° C., and then stirred at room temperature for 20 hours. After addition of water to the reaction product mixture, the resulting mixture was extracted with hexane. The organic phase thus separated was subjected to conventional work-up including washing, drying, and concentration to obtain a crude product containing a mixture (0.653 g, 3.36 mmol) of geometric isomers of 1,3-tetradecadiene and positional isomers with respect to the double bond (0.653 g, 3.36 mmol) as well as the starting material (E)-3-tetradecadienyl methoxymethyl ether (0.584 g, 2.28 mmol). It was confirmed by GC/MS that there were at least six tetradecadiene isomers. The geometry and position of the double bond were not able to be identified and the yield of (E)-1,3-tetradecadiene was not able to be calculated. The crude yield as a tetradecadiene isomer mixture was 28%.

Thus, in the substrate having a hydrocarbon group instead of the acetal group at the α-position of the double bond, elimination did not proceed efficiently.

Example 12

Production No. 1 of (E)-2,4-pentadienal (3)

In a nitrogen atmosphere, (Z)-5,5-diethoxy-1,3-pentadiene (77.5 g, 0.496 mol), toluene (632 g) and water (18 g) were placed in a reactor, stirred at from 0 to 10° C., subjected to dropwise addition of 20% hydrochloric acid (71 g) at from 0 to 10° C., and then stirred at from 0 to 10° C. for 3 hours. The pH value of the water phase was confirmed to be less than 1 with pH test paper. After addition of water to the reaction product mixture, the resulting mixture was neutralized with an aqueous solution of sodium hydroxide. The organic phase thus separated was subjected to conventional work-up including washing and drying to obtain a toluene solution (681 g) of intended (E)-2,4-pentadienal (3) (39.7 g, 0.483 mol) in a yield of 97%.

(E)-2,4-Pentadienal (3)

Colorless to Light Yellow Oily Liquid
IR (D-ATR): ν=2817, 2726, 1683, 1635, 1592, 1421, 1172, 1108, 1017, 997, 935, 853, 600 cm$^{-1}$.
$^1$H-NMR (500 MHz, CDCl$_3$): δ=5.60 (1H, dd, J=0.8, 19.9 Hz), 5.70-5.74 (1H, m), 6.12-6.16 (1H, m), 6.52-6.60 (1H, m), 7.05-7.10 (1H, m), 9.56 (1H, d, J=7.7 Hz) ppm.
$^{13}$C-NMR (125 MHz, CDCl$_3$): δ=127.45, 132.26, 134.73, 151.85, 193.65 ppm.

Example 13

Production No. 2 of (E)-2,4-pentadienal (3)

A toluene solution (681 g) of (E)-2,4-pentadienal (3) (39.7 g, 0.483 mol) was obtained in a yield of 97% in the same manner as in Example 12 except for the use of (E)-5,5-diethoxy-1,3-pentadiene (77.5 g, 0.496 mol) instead of (Z)-5,5-diethoxy-1,3-pentadiene (77.5 g, 0.496 mol).

Example 14

Production No. 1 of (Z)-2,4-pentadienal (3)

In a nitrogen atmosphere, (Z)-5,5-diethoxy-1,3-pentadiene (77.5 g, 0.496 mol), toluene (632 g) and water (261 g) were placed in a reactor, stirred at from 0 to 10° C., subjected to dropwise addition of 20% hydrochloric acid (1 g) at from 0 to 10° C., and then stirred at from 0 to 10° C. for 3 hours. The pH value of the water phase was confirmed to be 2 with pH test paper. After addition of water to the reaction product mixture, the resulting mixture was neutralized with an aqueous solution of sodium hydroxide. The organic phase thus separated was subjected to conventional work-up including washing and drying to obtain a toluene solution (681 g) of intended (Z)-2,4-pentadienal (3) (39.7 g, 0.483 mol) in a yield of 97%.

(Z)-2,4-Pentadienal (3)

Colorless to Light Yellow Oily Liquid
$^1$H-NMR (500 MHz, CDCl$_3$): δ=5.66-5.73 (2H, m), 5.97-6.01 (1H, m), 6.97-7.09 (1H, m), 7.25-7.40 (1H, m), 10.27 (1H, d, J=8.0 Hz) ppm.

Example 15

Production No. 2 of (Z)-2,4-pentadienal (3)

In a nitrogen atmosphere, (Z)-5,5-diethoxy-1,3-pentadiene (77.5 g, 0.496 mol), toluene (632 g), water (150 g) and acetic acid (5 g) were placed in a reactor. The pH value of the water phase was confirmed to be 3 with pH test paper. Then, the pressure was reduced to 150 mmHg, followed by stirring at 75° C. and distillation of ethanol for 3 hours. After addition of water to the reaction product mixture, the resulting mixture was neutralized with an aqueous solution of sodium hydroxide. The organic phase thus separated was subjected to conventional work-up including washing and drying to obtain a toluene solution (681 g) of intended (Z)-2,4-pentadienal (39.7 g, 0.483 mol) in a yield of 97%.

Example 16

Production of (2E,4E)-2,4-hexadienal (3)

In a nitrogen atmosphere, a 2Z4E:2Z4Z=73:27 geometrical isomer mixture of 1,1-diethoxy-2,4-hexadiene (8.44 g, 49.6 mmol), toluene (63 g) and water (2 g) were placed in a reactor, stirred at from 0 to 10° C., subjected to dropwise addition of 20% hydrochloric acid (7 g) at from 0 to 10° C., and then stirred at from 0 to 10° C. for 3 hours. The pH value of the water phase was confirmed to be less than 1 with pH test paper. After addition of water to the reaction product mixture, the resulting mixture was neutralized with an aqueous solution of sodium hydroxide. The organic phase thus separated was subjected to conventional work-up including washing and drying to obtain a toluene solution (68 g) of intended (2E,4E)-2,4-hexadienal (3) (4.64 g, 48.3 mmol) in a yield of 97%.

(2E,4E)-2,4-Hexadienal (3)

Colorless to Light Yellow Oily Liquid
$^1$H-NMR (500 MHz, CDCl$_3$): δ=1.92 (3H, d, J=5.2 Hz), 6.06 (1H, dd, J=7.9, 15.4 Hz), 6.18-6.44 (2H, m), 7.00-7.16 (1H, m), 9.54 (1H, d, J=7.9 Hz) ppm.

By deprotecting the 2,4-dienal acetal as described in Examples 12 to 16, a 2,4-dienal compound can be produced efficiently. In the deprotection by a hydrolysis reaction, a geometric isomer of a 2,4-dienal compound can be selectively produced by selecting the pH value of the aqueous solution in the reaction system as needed.

The invention claimed is:

1. A method for producing a 2,4-dienal acetal compound of Formula (2):

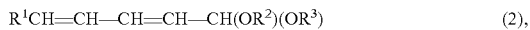

$$R^1CH=CH-CH=CH-CH(OR^2)(OR^3) \quad (2),$$

comprising a step of subjecting a 2-enal acetal compound having a leaving group X at position C5 and being expressed by Formula (1):

$$R^1CHX-CH_2-CH=CH-CH(OR^2)(OR^3) \quad (1),$$

wherein, R$^1$ stands for a hydrogen atom or a substituted or unsubstituted monovalent hydrocarbon group having from 1 to 13 carbon atoms, R$^2$ and R$^3$ each independently stands for a monovalent hydrocarbon group having from 1 to 10 carbon atoms, or R$^2$ and R$^3$ are joined together to form, as R$^2$-R$^3$, a divalent hydrocarbon group having from 2 to 10 carbon atoms, X stands for a leaving group which is an alkoxy group having from 1 to 12 carbon atoms, an acyloxy group having from 1 to 10 carbon atoms, a silyloxy group having from 3 to 20 carbon atoms, an alkanesulfonyloxy group having from 1 to 10 carbon atoms, an arenesulfonyloxy group having from 6 to 20 carbon atoms, or a halogen atom, to an elimination reaction in the presence of a base to obtain the 2,4-dienal acetal compound (2).

2. The method for producing a 2,4-dienal acetal compound according to claim 1, wherein the base is selected from the group consisting of a metal alkoxide, an organometallic reagent, a metal amide, a metal hydride, and an amine.

3. The method for producing a 2,4-dienal acetal compound according to claim 1, wherein the R$^1$ is a hydrogen atom.

4. A method for producing a 2,4-dienal compound of Formula (3):

$$R^1CH=CH-CH=CH-CHO \quad (3),$$

comprising steps of:

subjecting a 2-enal acetal compound having a leaving group X at position C5 and being expressed by Formula (1):

$$R^1CHX-CH_2-CH=CH-CH(OR^2)(OR^3) \quad (1),$$

wherein $R^1$ stands for a hydrogen atom or a substituted or unsubstituted monovalent hydrocarbon group having from 1 to 13 carbon atoms, $R^2$ and $R^3$ each independently stands for a monovalent hydrocarbon group having from 1 to 10 carbon atoms or $R^2$ and $R^3$ are joined together to form, as $R^2$-$R^3$, a divalent hydrocarbon group having from 2 to 10 carbon atoms, X stands for a leaving group which is an alkoxy group having from 1 to 12 carbon atoms, an acyloxy group having from 1 to 10 carbon atoms, a silyloxy group having from 3 to 20 carbon atoms, an alkanesulfonyloxy group having from 1 to 10 carbon atoms, an arenesulfonyloxy group having from 6 to 20 carbon atoms, or a halogen atom, to an elimination reaction in the presence of a base obtain a 2,4-dienal acetal compound of Formula (2):

$$R^1CH=CH-CH=CH-CH(OR^2)(OR^3) \quad (2); \text{ and}$$

deprotecting the 2,4-dienal acetal compound (2) to obtain the 2,4-dienal compound (3).

5. The method for producing a 2,4-dienal compound according to claim 4, wherein the base is selected from the group consisting of a metal alkoxide, an organometallic reagent, a metal amide, a metal hydride, and an amine.

6. The method for producing a 2,4-dienal compound according to claim 4, wherein the $R^1$ is a hydrogen atom.

7. The method for producing a 2,4-dienal acetal compound according to claim 2 wherein the $R^1$ is a hydrogen atom.

8. The method for producing a 2,4-dienal compound according to claim 5, wherein the $R^1$ is a hydrogen atom.

* * * * *